(12) United States Patent
Schulze et al.

(10) Patent No.: US 6,556,852 B1
(45) Date of Patent: Apr. 29, 2003

(54) EARPIECE WITH SENSORS TO MEASURE/ MONITOR MULTIPLE PHYSIOLOGICAL VARIABLES

(75) Inventors: Arthur E. Schulze, Wharton, TX (US); Tommy G. Cooper, Friendswood, TX (US)

(73) Assignee: I-Medik, Inc., Santa Fe, NM (US)

( * ) Notice: Subject to any disclaimer, the term of this patent is extended or adjusted under 35 U.S.C. 154(b) by 0 days.

(21) Appl. No.: 09/818,035

(22) Filed: Mar. 27, 2001

(51) Int. Cl.[7] .................................................. A61B 5/00
(52) U.S. Cl. ..................... 600/323; 600/459; 600/310; 600/340; 600/341; 600/344; 600/322
(58) Field of Search ................................ 600/459, 323, 600/344, 310, 322, 339, 340, 341

(56) References Cited

U.S. PATENT DOCUMENTS

| | | | |
|---|---|---|---|
| 5,626,139 A | * 5/1997 | Szeles et al. | 128/664 |
| 5,673,692 A | * 10/1997 | Schulze et al. | 128/633 |
| 6,047,205 A | * 4/2000 | Pompei | 600/474 |
| 6,254,526 B1 | * 7/2001 | Juneau et al. | 600/25 |

* cited by examiner

Primary Examiner—Teresa Walberg
Assistant Examiner—Shawntina Fuqua
(74) Attorney, Agent, or Firm—Roberts Abokhair & MArdula, LLC

(57) ABSTRACT

An apparatus and method for positioning sensors relative to one another and anatomic features in a non-invasive device for measuring and monitoring multiple physiological variables from a single site uses an earpiece incorporating a shielded pulse oximetry sensor (POS) having a miniaturized set of LEDs and photosensors configured for pulse oximetry measurements in the reflectance mode and located in the earpiece so as to position the POS against a rear wall of an ear canal. The earpiece also includes a thermopile of no larger than 7 mm. in diameter located on the earpiece to so as to position the thermopile past a second turn of an external auditory meatus so as to view the tympanic membrane. The thermopile includes a reference temperature sensor attached to its base for ambient temperature compensation.

5 Claims, 6 Drawing Sheets

EARPIECE WITH SENSORS TO MEASURE/MONITOR MULTIPLE PHYSIOLOGICAL VARIABLES

GOVERNMENT LICENSE RIGHTS

The U.S. Government has a paid-up license in this invention and the right in limited circumstances to require the patent owner to license others on reasonable terms as provided by the terms of contract no. NAS 9-99029 awarded by the National Aeronautics & Space Administration (NASA).

FIELD OF THE INVENTION

The present invention relates generally to the fields of physiological measurements. More particularly, this invention relates to a method and apparatus to position sensors for non-invasively measuring and/or monitoring two or more physiological variables using a miniaturized device that fits in the ear canal of a subject, generating data that is acquired, stored, displayed, and controlled using custom software. There is a particular need for this invention for the continuous monitoring of physiological variables in subjects (such as NASA crew members) who need to be unencumbered and ambulatory.

The present Invention discloses a discrete, non-invasive device capable of measuring/monitoring two or more clinically relevant physiological variables, and unobtrusively providing continuous data for these variables. The raw data thus generated is acquired, stored and displayed to yield meaningful values for clinically relevant physiological variables.

BACKGROUND INFORMATION

Current commercial practice does not adequately address specific issues that the present invention has been designed to resolve: simultaneous core temperature, arterial blood oxygen saturation, and pulse rate with minimal intrusiveness. Core Body Temperature:

This variable is commonly measured using thermometers that are placed sublingually, rectally, and via the axilla (armpit). Sublingually placed thermometers are not very convenient or comfortable, cannot be left in place for prolonged periods or for continuous temperature measurements, and can be bitten by patients. Rectal thermometers, because of their invasive nature, are generally disliked by subjects who are awake and alert axillary temperature measurements are also inconvenient, requiring the subject to posture unnaturally, and are not as accurate as measurements taken from the ear.

In the 1960s, researchers began to explore the ear canal and its structures (particularly the tympanic membrane, or eardrum) as a site for core body temperature readings. The tympanic membrane shares its blood supply with the hypothalamus (the body's thermostat), making it a uniquely desirable site for core temperature measurement. Methods for continuously measuring core body temperature via the ear have involved placing a thermistor or thermocouple against the subject's tympanic membrane/ear canal wall (the sensor makes actual contact with these structures). This procedure has been used in assessing the core body temperature of critically burned patients, who are generally unconscious or anaesthetized. However, this method is not very popular for use in subjects who are awake and alert as it can be uncomfortable, inconvenient, and injurious (possibly resulting in eardrum perforation).

Less invasive technology has been developed, exploiting the fact that thermal energy can be detected and quantified using an infrared sensor Researchers have investigated and developed infrared thermometry as a means to measure infrared emission from the tympanic membrane, without making actual contact with the membrane. This method has numerous advantages, since it is extremely accurate, can be done within seconds, (as there is no need for surface-to-surface thermal equilibrium), does not carry the risk of eardrum puncture, and does not require unnatural posturing by the subject. Moreover, subjects can tolerate the placement of an IR thermometer in the ear canal for long periods of time, allowing continuous measurements of core body temperature. Commercial technology exists for each of the elements of an offset tympanic membrane temperature monitor; however, none of them are known to be able to operate continuously at an ambient temperature different from the measurement site temperature by only a few degrees.

Arterial Blood Oxygen Saturation and Pulse Rate

Pulse oximeters are available to operate by both transmission and reflectance modalities. These devices, which non-invasively measure the oxygen saturation of hemoglobin in the blood, are among the most universally utilized monitoring instrumentation in today's hospital. Advantageously, the transduced signal also contains beat-by-beat pulse rate information. In many subjects, though by no means 100%, the sinus arrhythmia related to breathing is so pronounced that measurements of changes in the beat-to-beat rhythm of the heart can also be used to derive respiration rate.

However, the present state of the art does little to address the challenge of providing continuous, accurate measurements of multiple physiological variables using a single site on the body, and permitting the subject to be ambulatory and unencumbered.

Therefore, there is a real need for a device that fits in the ear, continuously generating accurate values for multiple physiological variables. Such a device would be very useful in a NASA space-exploration setting, during physical rehabilitation, and in other settings that require a subject to be ambulatory and unencumbered while vital physiological variables are measured/monitored.

BRIEF SUMMARY OF THE INVENTION

The present invention is drawn to a system that acquires multiple variables of meaningful, clinically-relevant physiological data from a single location on the human body in an unobtrusive, non-invasive manner. The invention includes the positioning of sensors relative to one another and to nearby anatomic structures in a system needed to acquire core temperature, arterial blood oxygen saturation, and pulse rate simultaneously and continuously from a location in the human ear canal.

The present invention provides a significant improvement to the prior art, in that it devises a means by which two (or more) clinically relevant variables can be measured using one discrete, unobtrusive device. The invention positions an infrared temperature sensor for measuring core body temperature and a pulse oximeter sensor ("POS") in a geometry capable of measuring/monitoring the oxygen saturation, heart rate, and core temperature of ambulatory, unencumbered subjects. The invention makes use of miniaturized sensors and circuitry, miniature thermopiles and spectrally matched optoelectronic devices.

Applications of the invention are numerous and include the monitoring of NASA crewmembers during EVA and exercise. The single site monitor allows a new measure of accuracy for continuous core temperature measurements during potential heat stress situations. It will also allow early detection of distress which causes changes in the cardiopulmonary variables of pulse rate and blood oxygen saturation. Commercial applications are also numerous and are generally associated with patient monitoring during surgical procedures, diagnostic procedures, alternate care facility activities, etc. A unique niche market requiring all of the features of the innovation is the monitoring of patients with Chronic Obstructive Pulmonary Disease (COPD).

The simultaneous operation of an infrared temperature sensor together with a pulse oximeter in the ear canal is not a trivial problem. U.S. Pat. No. 5,673,692, co-invented by the present inventors and herein incorporated in its entirety by reference, discloses a basic infrared temperature sensor together with a pulse oximeter in the ear canal, but does not disclose a system for practically solving temperature compensation and sensor interference problems associated with using such a device.

The solution requires some sensor selection, sequencing control, time-division multiplexing, and aiming geometry innovations to prevent thermal interference during long-term monitoring. It also requires precise placement to prevent motion artifacts when patients chew food or speak. Whereas, commercially, it is necessary that the sensor housing fit as wide a range of patient ear anatomical configurations as possible, the use of a custom ear mold to optimize performance of the sensor on NASA EVA crewmembers is desirable.

The approach to the present invention is to solve practical design problems in combining infrared temperature measurements of core temperature from the tympanic membrane with pulse oximetry from the ear canal.

It is an object of the invention to provide a system to position sensors with respect to each other and anatomical structures to prevent thermal interference during acquisition of core temperature, arterial blood oxygen saturation, and pulse rate simultaneously and continuously from a location in the human ear.

It is an object of the invention to position a temperature sensor in a manner that is not vasoactive.

It is another object of the invention to monitor multiple physiological variables from a single site with minimal restriction of patient sensory experiences.

It is another object of the invention to monitor multiple physiological variables from a stabilized location with minimal patient motion artifact generation.

It is yet another object of the invention to monitor multiple physiological variables from a protected location with minimal potential for instrument/sensor damage.

It is yet another object of the invention to monitor multiple physiological variables from a single site with minimal patient objections to site location and ease of use by both males and females.

It is a further object of the invention to monitor multiple physiological variables from a single site using a single ear mold to fit a large range of population.

It is another object of the invention to monitor multiple physiological variables from a single site with simple attachment to a subject and rapid stabilization of data acquisition.

It is another object of the invention to monitor multiple physiological variables from a single site with quick or no calibration requirements.

It is yet another object of the invention to monitor multiple physiological variables from a single site that is useful continuously for at least 24 hours without removal.

It is yet another object of the invention to monitor multiple physiological variables from a single site with low-cost components for commercial feasibility.

DETAILED DESCRIPTION OF THE INVENTION

Figure 1:
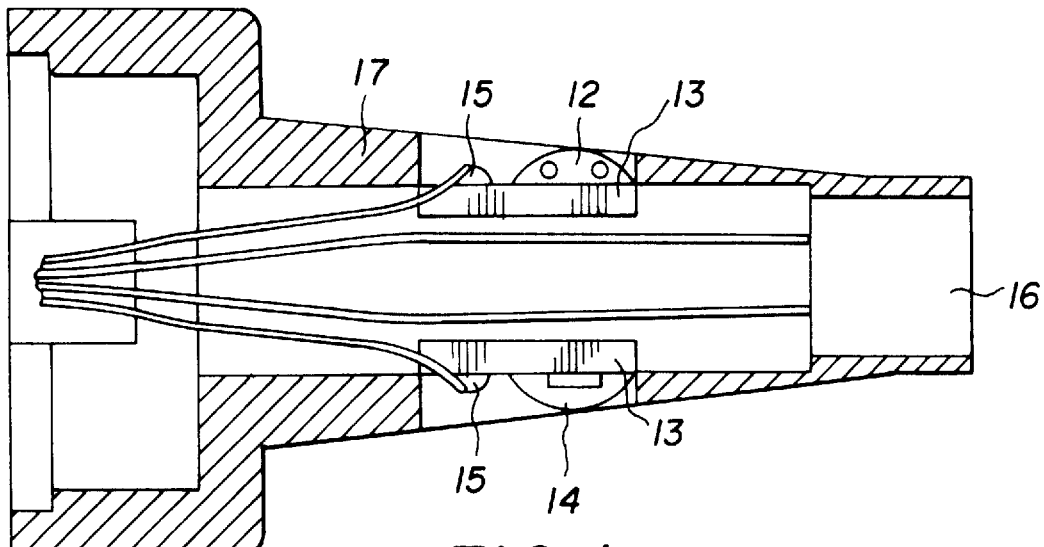
FIG. 1 illustrates general location of the sensors of the present invention.

FIG. 1 illustrates the general location of the sensors, but does not show the curvature required to comfortably fit in the ear canal. The LEDs 12 and the photosensor 14 must be aligned to cover the same tissue such that the illuminated tissue can be "seen" by the photosensor 14. Since the depth of penetration of human tissue by the infrared wavelength varies from that at the red wavelength, it is best if the tissue is constrained to a given depth by some inhomogeneity such as bone or cartilage. These conditions can be met in the human ear canal and this enables the further development of multivariable sensors suitable for use in the human ear.

One of the most difficult parts of designing the present invention was locating, pointing, and holding the sensors at sites in the ear canal that demonstrate minimum artifact production during motion (generally most severe during eating and chewing). Additionally, selection of sensor components that were small enough to make the overall sensor feasible was also a major part of the present invention.

The earpiece sensor configuration must locate and hold two light-emitting diodes (LEDs) 12 and one photosensor 14 which must be imbedded in physiologically inert and soft material 17 and inserted into the ear canal. A miniature IR sensor 16 (thermopile with IR filter) must be contained within the earpiece and aimed at the tympanic membrane. This requires that the sensor be designed to hold the active face of the IR sensor 16 deep enough within the ear canal that it can "view" the tympanic membrane (ear drum) directly without contacting it. Such a position involves using a curved earpiece that will allow position the sensor 16 around the bends in a normal adult ear canal.

Extensive research was conducted to select a pulse oximeter module that would perform adequately with the low signals that are found in the reflectance mode. It is also important that this circuitry be small, power efficient, and contain the necessary dynamic range and speed of response to support rapid changes that might occur in the active subject and the crewmember in EVA activities.

There are over a dozen manufacturers of pulse oximeters in the U.S. and each device has its own unique characteristics. Sample devices were obtained from four different manufacturers during the course of this research. Each device was evaluated for performance, recovery time from motion artifacts, power consumption, size, and weight. The OEM II Pulse Oximetry Module by Nonin Medical, Inc. (Plymouth, Minn.) measures only 1.35"×1.8"×0.36" and weighs only 12 grams, including static and RF shielding. The power consumption is about 75 mW, and can be considerably less through the use of time-division-multiplexing techniques. Development software available with the kit detects sensor errors and loss of signal. This continuous self-test feature is has obvious utility. The module operates from 5 volts DC and contains patient electrical isolation greater than 12 megohmsIt is rated for use over the full range of oxygen saturation and over a pulse rate range of 15 to 300 pulses per minute at operating temperatures between 0 and +50 degrees C.

The pulse oximeter is designed to work with a variety of probes, both transmissive and reflective. The miniature LEDs 12 used in these probes emit red light at a wavelength of 660 nanometers and infrared light at a wavelength of 910 nanometers. The photosensor 14 is also a miniature device which is used to detect both wavelengths. These signals are processed to determine pulse rate by detecting the change in blood volume in the tissue and they are processed to determine the percentage oxygen saturation in arterial blood by standardized ratiometric methodology.

The disposable sensors contain miniature LEDs 12 and photosensors 14 that are mounted on small ceramic substrates 13 that allow solder connections 15. These devices are small enough to be used to fabricate various models of the ear-mounted sensors. The present invention can be further miniaturized by use of the elements alone, independent of the ceramic substrates 13.

The pulse oximeter LEDs 12 and photosensor 14 must be located in firm, direct contact with vascularized and well-perfused tissue that is preferably covering a cartilage or bone substrate. It was discovered that an ideal location for these sensors is in the external auditory canal facing toward the back of the head. The exact location was determined by testing various configurations for susceptibility to motion artifacts, especially those resulting from talking and chewing. A minimum-noise location was one of the key findings of this research. The sensors must be shielded from both stray light and electromagnetic interference.

The continuous infrared thermometer of the present invention requires the selection of a sensor and optical filter to cover the range of temperatures and wavelengths desired. The use of a miniature thermopile (a voltage-generating device comprised of an array of thermocouple junctions located behind a layer of a heat-absorbing material) was determined to be the best device to use for the present invention. Although the number of companies that manufacture thermopiles meeting the sensitivity and size constraints is very limited, a preferred, cost effective sensor was selected from UniTra Korea, Inc.

Figure 2:
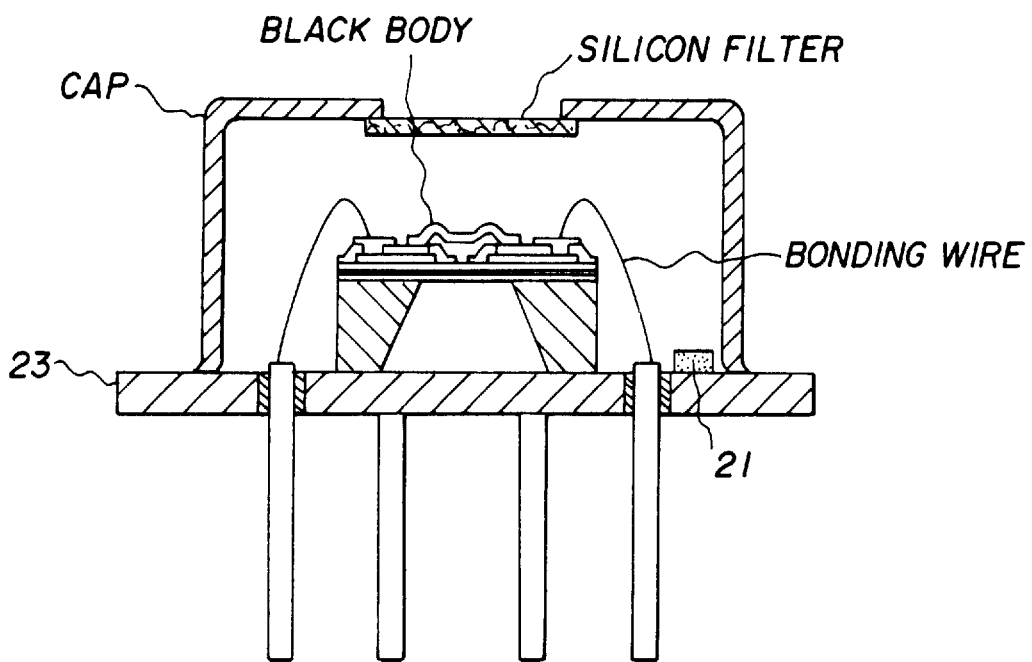
FIG. 2 illustrates a preferred thermopile for use with the present invention.

Their MemTek ThermopileIR Sensor LGTP-205S sensor is packaged in a TO-46 transistor-type package and contains 36 thermocouples on a chip of 1.9 mm by 2.0 mm. The length of the package is only 3.2 mm. One of the unique features of the LGTP-205S is the built-in thermistor 21 which is mounted on the base 23 and used for ambient temperature compensation, as illustrated in FIG. 2. This thermistor 21 eliminates the need for the secondary operation of attaching an external thermistor or thermocouple to the package.

The thermopile sensor must be inserted into the ear canal just past the second turn of the external auditory meatus to place the tympanic membrane in its field of view. Determining the optimum location of the sensors in the earpiece and devising how to place them there and secure them so that they can be worn comfortably were some of the most difficult tasks of developing the present invention.

The location of the pulse oximetry sensors (POS) was determined empirically, based upon signal amplitude and artifact rejection criteria. It was found that the POS were best located on the side of the ear canal away from the temporomandibular joint, pointed such that they overlap an adequate amount of tissue to generate sufficient signals for the pulse oximetry to process using reflective techniques. This location was first probed using flexible material and was then confirmed using custom acrylic earmolds.

The location of the IR thermometer (thermopile) was also determined empirically by the analysis of earmolds used for hearing aids. It was determined that the maximum diameter of the thermopile element that can comfortably fit into most ears is 7 mm. This size will allow a minimum amount of material surrounding the thermopile sensor, but it confirms that a 5-mm-diameter device is not too large for use in this manner.

Figure 3:
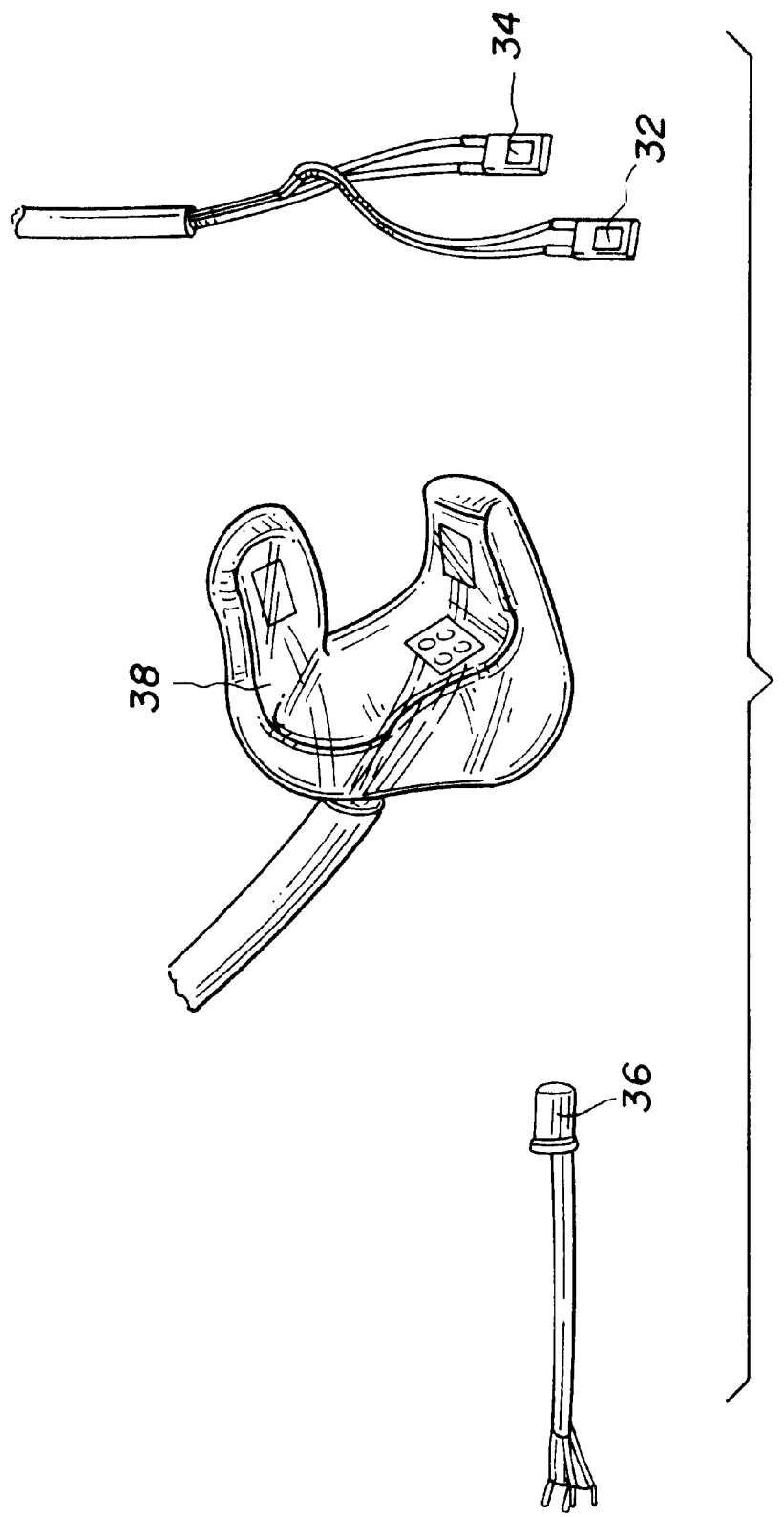
FIG. 3 illustrates a custom earpiece and sensor components in accordance with the present invention.

As for thermopile depth, the requirements of a direct view of the tympanic membrane is similar to that required by hearing aids. It is well known by audiologists that a hearing aid must be fitted to a depth that allows the porting of sound directly at the tympanic membrane and this involves a curved holder that will place the active element on the inside of the first curve of the ear canal. FIG. 3 illustrates a suitable custom earpiece 38 and the sensors contained within it. On the left side is a thermopile sensor 36 and on the right side are the LEDs 32 and photosensor 34 with lead wires attached.

Materials used to fabricate the earpiece are also part of the present invention. The materials must be rigid enough to protect the sensors and to hold them in the proper position, yet be soft enough to allow a comfortable fit in the active subject. The ear canal also contains secretions such as cerumen (ear wax) and expressed moisture. Long-term use of earpieces requires consideration of the effects that such secretions might have on the device.

Several materials, both hard and soft, have been tested. Acrylic and silicone formulations dominated the testing. It was found that a transparent material has some definite advantages because it allows inspection of the internal components and wiring.

Three different designs for earpieces were identified as follows:
  A custom earpiece fabricated for an exact fit of the patient or subject;
  A "one size fits most" earpiece for general application on a variety of patients or subjects; and
  A disposable configuration using adaptor pieces, if necessary, to fit any patient or subject for short-term use.

Figure 4:
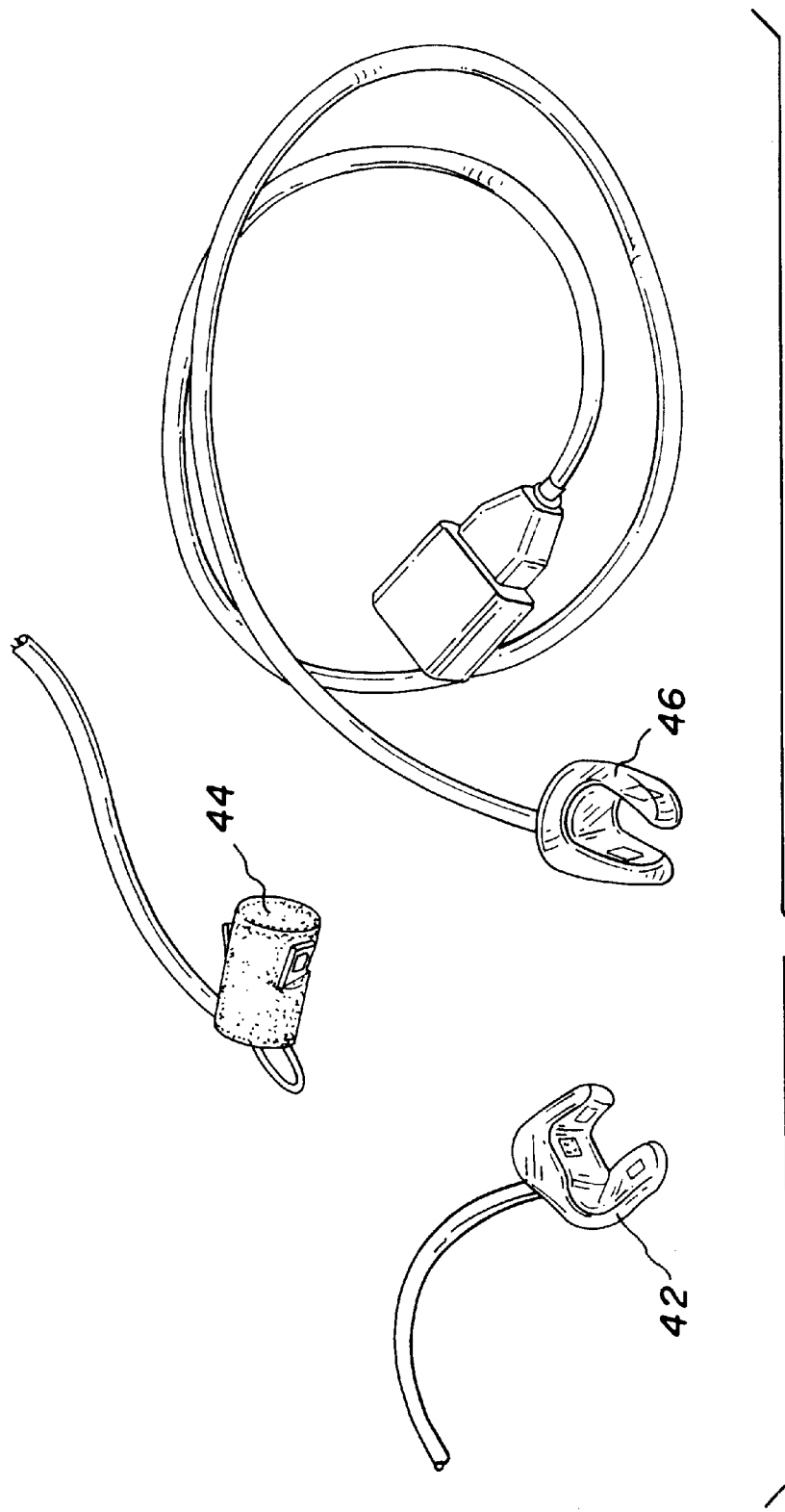
FIG. 4 illustrates various earpieces for use with the present invention.

FIG. 4 illustrates the three different earpieces. On the left is the custom earpiece 42. In the middle is the disposable earpiece 44 and on the right is the "one size fits most" earpiece 46.

For those applications requiring the best possible fit, such as for NASA EVA, custom earpieces 42 are the preferred embodiment. This is easily accomplished by taking a cast of the ear and fitting the sensors in the best possible location to customize the earpiece for the subject or patient. This type of sensor might also be the best selection for those patients who will be monitored continuously for long terms. It is the most comfortable configuration. Techniques for making impressions and casting custom earmolds are ubiquitous, and some of them allow fabrication immediately, on-site.

For general applications in long-term, continuous monitoring, a "one size fits most' configuration 46 can be used. It involves the use of standardized soft earpieces which are usually used with temporary hearing aids that are remote from the ear. Such pieces are also commonly used in commercial telephone headsets where they must fit a wide range of ear sizes and shapes. These earpieces obviously do not fit as well as customized earpieces, but their performance under routine, temporary circumstances is adequate. In some instances, a small shim of silicone material should be used to maintain contact between the oximetry sensors and the ear canal.

For general application in short-term clinical monitoring, a disposable configuration 44 was developed. Usually, the disposal of the complete sensor assembly will not be economically feasible, but in situations where the risk of cross contamination is severe, the cost may not be a critical issue. An alternative to disposable sensor assemblies is the use of clear protective sheaths that can be removed and thrown away after each use.

In clinical monitoring situations, standard procedures for the use of the earpiece will involve inspection of the patient's ear canal for skin condition and presence of ear wax. Routine procedures may also involve the use of over-the-counter ear wax removal solutions prior to the placement of the earpiece.

Figure 5:
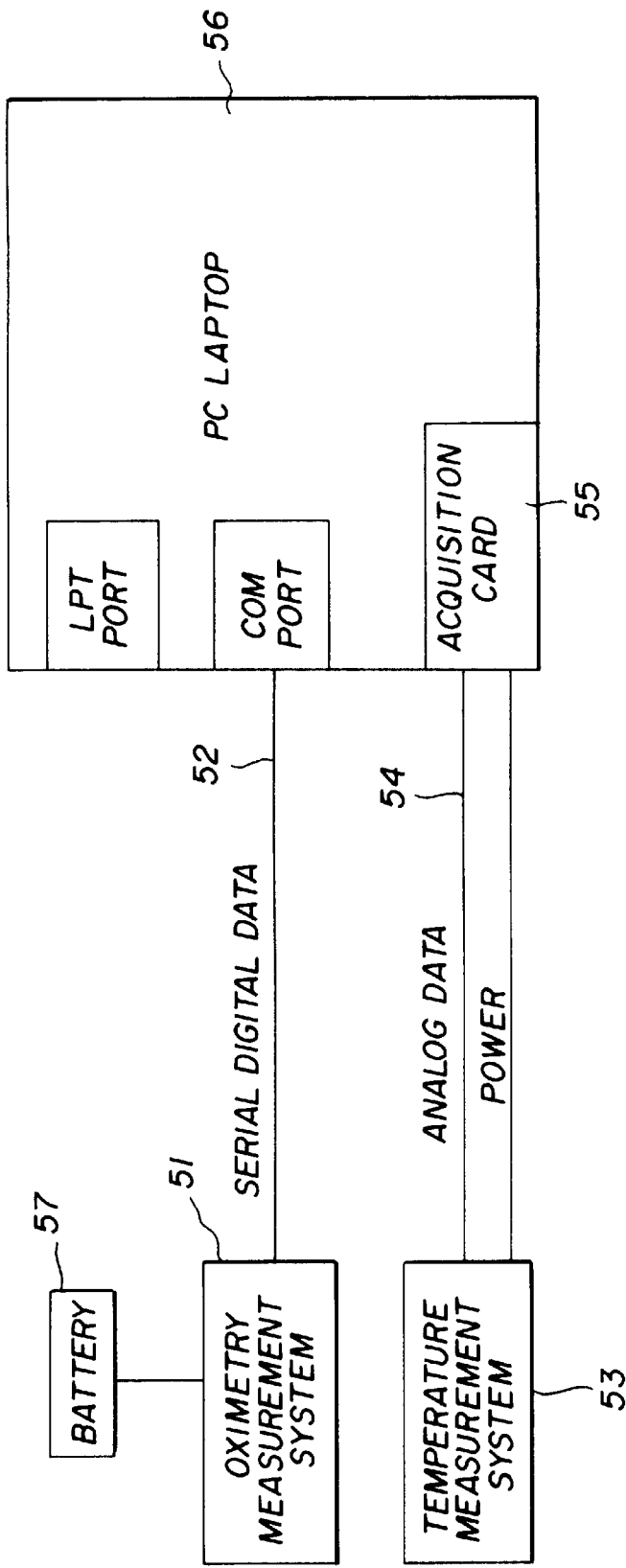
FIG. 5 illustrates a hardware block diagram of the present invention.

The data acquisition hardware of the present invention consists of a Pulse Oximetry Module and interface card, such as a Nonin Medical #2332-000 OEM Pulse Oximetry Module, a data acquisition and interface means, such as a National Instruments #777087-01 DAQ and Multifunction I/O Card, and a suitable infrared thermometer interface. National Instruments' LabWindows/CVI Integrated C Development Environment for Scientists and Engineers was used to develop the software for the virtual instrument, although this is not meant as a limitation. A basic block diagram of the hardware is illustrated in FIG. 5.

In a preferred embodiment, the Oximetry Measurement System 51 is a Nonin Medical OEM Module mounted on an interface card with a serial data output 52 at 9,600 Baud, 8 data bits, 1 start bit, 1 stop bit, and 3 bytes of data per second. This subsystem provides built-in continuous self-test capability, which detects and displays sensor errors.

Figure 6:
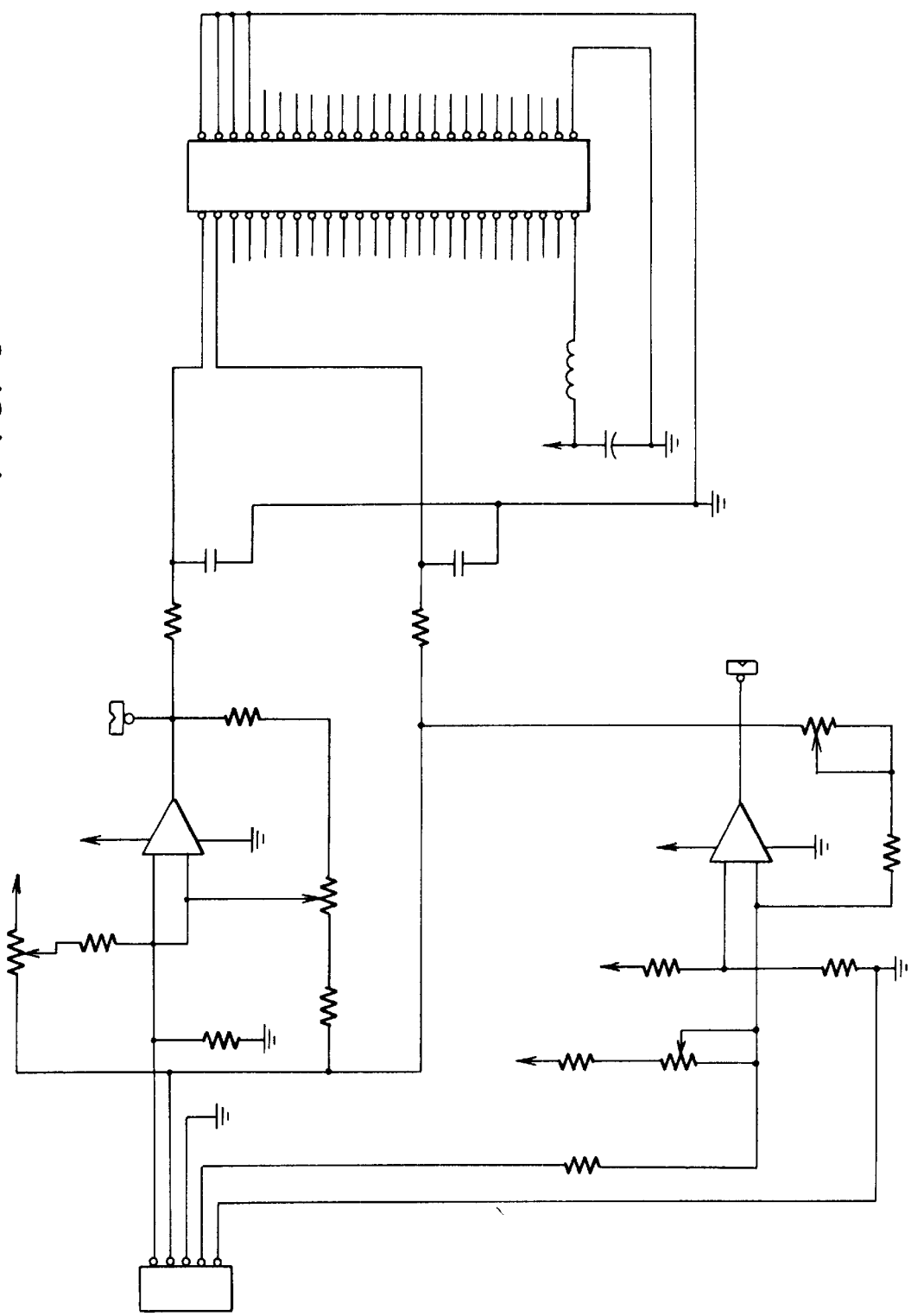
FIG. 6 illustrates a suitable infrared temperature interface card diagram for use with the present invention.

The Temperature Measurement System 53 provides the analog interface 54 to the thermopile detector and provides ambient temperature compensation for the base of the sensor. The output of this card is preferably digitized by a 12-bit A/D converter located in a PCMCIA card 55 interfaced to a PC Laptop (or desktop) computer 56. The external interface cards are battery-powered 57. A schematic diagram of a suitable infrared temperature interface card is illustrated in FIG. 6.

Figure 7:
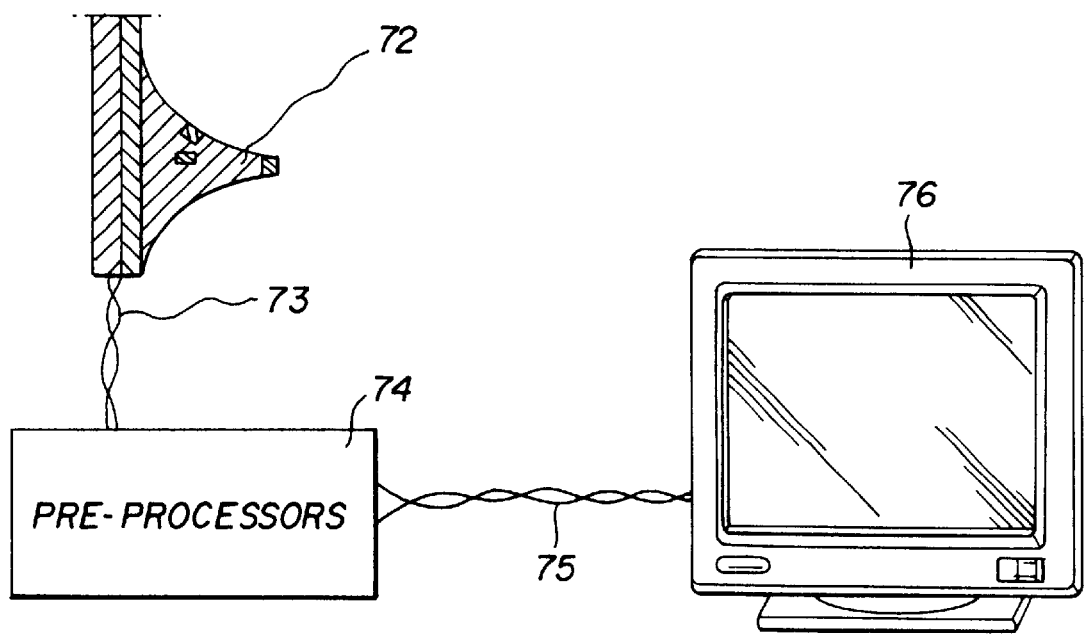
FIG. 7 illustrates the system components in accordance with a first embodiment of the present invention.

A virtual instrument of the present invention is illustrated in FIG. 7.

Real-time display of the following data is provided at a display speed selected by the operator:
  Arterial Blood Oxygen Saturation (%)
  Cardiac Pulse Rate (beats per minute)
  Tympanic Membrane (Core) Temperature (degrees F. or degrees C.).

An alternative display of long-term trend information for each variable is provided with a selection of sample rates and display speeds that can be changed by the operator while the display is active.

All data displayed by the virtual instrument can also be stored for analysis at a future date. Downloaded data stored in the PC can be placed into spreadsheet applications and printed. Time stamps are provided on all data.

As part of the present invention, virtual instrument display which can be manipulated and controlled by the operator was developed for display on a PC. The instrument was configured such that it can be used with either hard-wired or wireless sensors. As mentioned earlier, LabWindows was used to develop a C-language program that can run under Win 95 or Win 98. The operator can control the speed of the chart display and can make hardcopies of the output. On-line help is provided for the operator.

A preferred embodiments comprises:
  Earpiece 72 containing pulse oximetry and tympanic temperature sensors;
  Battery-powered pre-processing circuitry 74 containing the pulse oximeter and temperature pre-processors;
  Small, flexible cable 73 to connect earpiece to electronics module;
  Data acquisition cable 75 or wireless bio-telemetry link to connect preprocessing
  circuitry to data acquisition card in PC 76; and
  Data Acquisition Card and software not shown).

Utilization of these items requires a PC computer with provisions to accommodate a PCMCIA card, although this is not meant as a limitation.

Below are the typical specifications for practice of the present invention:
Sensors
Pulse Oximetry
  A miniaturized set of LEDs and photosensors are configured for pulse oximetry measurements in the reflectance mode. The duty cycle of this instrument is reduced to minimize tissue heating and conserve power. Instrument is shielded as required to reduce stray light and electromagnetic interference. The sensors face the rear wall of the ear canal.
Infrared Thermometer
  This instrument includes a miniature thermopile which will fit into the adult ear to a depth where the tympanic membrane can be visualized (5 mm. diameter maximum). The optical filter selected has a passband optimized for tissue temperature measurements. In addition, the device includes a reference temperature sensor attached to the base of the thermopile for ambient temperature compensation. The thermometer is calibrated using blackbody techniques
Earpieces
  The earmold probe for the thermopile is no larger than 7 mm. in diameter to insert into the adult ear canal to a position just past the second turn of the external auditory meatus. There is an earmold insert for the pulse oximetry sensor that will position the sensors against the rear wall of the ear canal. This device uses materials that are rigid enough to protect the sensors and hold them in the proper position, yet soft enough to allow a comfortable fit, that are resistant to cerumen and expressed moisture in the ear canal, and that are transparent to allow visual inspection of internal components.

We claim:

1. A configuration of sensors in a non-invasive emplacable device for continuously measuring and monitoring multiple physiological variables from a single site, comprising:
  an earpiece having a curve;
  a pulse oximetry sensor having a miniaturized set of LEDs and photosensors configured for pulse oximetry measurements in the reflectance mode and located in said earpiece so as to position said pulse oximetry sensor against a rear wall of an ear canal upon earpiece insertion to reduce noise from motion artifacts;

a thermopile of no larger than 7 mm. in diameter located on said earpiece beyond said curve in said earpiece so as to position said thermopile past a second turn of an external auditory meatus of said ear canal upon insertion so as to view a tympanic membrane, said thermopile further including a reference temperature sensor attached to a base portion of said thermopile for ambient temperature compensation; and a shield positioned within said earpiece to block stray light and electromagnetic interference.

2. The apparatus of claim 1, wherein said earpiece is custom-fit and formed of acrylic.

3. The apparatus of claim 1, wherein said earpiece is universal and formed of silicone.

4. The apparatus of claim 1, wherein said earpiece includes a silicone shim.

5. The apparatus of claim 1, wherein said reference temperature sensor is a thermistor.

* * * * *